United States Patent [19]

Bauer

[11] Patent Number: 5,302,531
[45] Date of Patent: Apr. 12, 1994

[54] COMPOSITION FOR THE SEMIQUANTITATIVE DETERMINATION OF SPECIFIC GRAVITY OF A TEST SAMPLE

[75] Inventor: Robert Bauer, Bristol, Ind.

[73] Assignee: Miles Inc., Elkhart, Ind.

[21] Appl. No.: 964,873

[22] Filed: Oct. 22, 1992

[51] Int. Cl.$^5$ ............................................. G01N 33/20
[52] U.S. Cl. ......................................... 436/74; 436/79; 436/84
[58] Field of Search ...................... 422/58; 436/66, 79, 436/169, 170, 74, 84

[56] References Cited

U.S. PATENT DOCUMENTS

| | | | |
|---|---|---|---|
| 3,975,161 | 8/1976 | Suoboda et al. | 436/66 X |
| 4,076,502 | 2/1978 | Dugle et al. | 422/58 X |
| 4,318,709 | 3/1982 | Falb et al. | 436/163 |
| 4,376,827 | 3/1983 | Stiso et al. | 436/169 X |
| 4,383,043 | 5/1983 | Denney et al. | 436/74 |
| 4,473,650 | 9/1984 | Wang | 436/169 X |
| 4,532,216 | 7/1985 | Wang | 436/169 X |
| 4,587,220 | 5/1986 | Mayabala-Minanika et al. | 436/66 |
| 4,871,679 | 10/1989 | Tanaka et al. | 436/170 X |
| 4,959,305 | 9/1990 | Woodrum | 436/170 X |
| 4,960,710 | 10/1990 | Lau | 436/169 X |
| 4,966,784 | 10/1990 | Tanaka et al. | 436/79 X |
| 5,055,407 | 10/1991 | Lau et al. | 436/169 X |
| 5,064,615 | 11/1991 | Mangold et al. | 436/169 X |
| 5,087,575 | 2/1992 | Lau | 436/169 X |
| 5,089,420 | 2/1992 | Albarella et al. | 436/169 X |
| 5,106,752 | 4/1992 | Mangold et al. | 436/169 X |

FOREIGN PATENT DOCUMENTS 0349934 7/1989 European Pat. Off. .

OTHER PUBLICATIONS

DeArmond et al., "Luminescence of Transition Metal d$^6$ Chelates", The Journal of Chemical Physics, vol. 54, (5), Mar. 1971 pp. 2247-2253.

Primary Examiner—James C. Housel
Assistant Examiner—Milton I. Cano
Attorney, Agent, or Firm—Roger N. Coe

[57] ABSTRACT

A method, composition and test device for the semi-quantitative determination of specific gravity of a test sample are disclosed. The method utilizes a reagent composition capable of producing a detectable and measurable response that correlates to the concentration of cations, and therefore the specific gravity, of the test sample. The reagent composition, comprises: a) a complexing agent, like a polyelectrolyte, an ion exchange material or a chelating agent, such as a copolymer of maleic acid and methyl vinyl ether; b) a polyvalent metal ion having a valence of at least two, like ferrous ion or cobaltous ion; c) an indicator capable of interacting with the polyvalent metal ion to provide a color transition, like calmagite or gallocyanine; and d) a suitable carrier. The reagent composition is used in a wet phase specific gravity assay or is incorporated into a carrier matrix, like filter paper, to provide a test pad useful in a dry phase specific gravity assay of a test sample, such as urine.

16 Claims, No Drawings

COMPOSITION FOR THE SEMIQUANTITATIVE DETERMINATION OF SPECIFIC GRAVITY OF A TEST SAMPLE

FIELD OF THE INVENTION

The present invention relates to a method, composition and test device for the semiquantitative determination of specific gravity of a test sample. More particularly, the present invention relates to a semiquantitative method of assaying an aqueous test sample, such as urine, for specific gravity utilizing a reagent composition that undergoes a detectable or measurable response as a result of contact between the test sample and the reagent composition, wherein the response is essentially independent of test sample pH. The detectable response is proportional to the cation concentration of the test sample and can be correlated to the specific gravity of the test sample. The reagent composition provides sufficient color differentiation between test samples having different specific gravities to provide a semiquantitative assay for the specific gravity of the test sample.

BACKGROUND OF THE INVENTION AND PRIOR ART

The specific gravity of a test sample, such as urine or serum, is a measure of the relative proportions of solid material dissolved in the test sample to the total volume of the test sample. In general, the specific gravity of a test sample is a measure of the relative degree of concentration or the relative degree of dilution of the test sample. With regard to urine samples, the assay for specific gravity, either quantitative or semiquantitative, helps interpret the results of the other assays performed in a routine urinalysis.

Clinically, under appropriate and standardized conditions of fluid restriction or increased fluid intake, the specific gravity of a urine sample measures the concentrating and diluting abilities of the kidneys of an individual. The specific gravity of urine ranges from about 1.005 to about 1.030, and usually is in the range from about 1.010 to about 1.025. A specific gravity of about 1.025 or above in a random first morning urine specimen indicates a normal concentrating ability of the kidneys.

Either an abnormally low or an abnormally high urine specific gravity is clinically significant. Therefore, accurate and reliable specific gravity assays of urine and other aqueous test samples must be available for both laboratory and home use. The assays must provide an accurate measurement of abnormally low and abnormally high specific gravities, such that a correct diagnosis can be made and correct medical treatment implemented, monitored and maintained.

For example, diabetes insipidus, a disease caused by the absence of, or impairment to, the normal functioning of the antidiuretic hormone (ADH), is the most severe example of impaired kidney concentrating ability. This disease is characterized by excreting large urine volumes of low specific gravity. The urine specific gravity of individuals suffering diabetes insipidus usually ranges between 1.001 and 1.003. Low urine specific gravity also occurs in persons suffering from glomerulonephritis, pyelonephritis, and various other renal anomalies. In these cases, the kidney has lost its ability to concentrate the urine because of tubular damage.

An abnormally high urine specific gravity also is indicative of a diseased state. For example, the urine specific gravity is abnormally high in an individual suffering from diabetes mellitus, adrenal insufficiency, hepatic disease or congestive cardiac failure. Urine specific gravity likewise is elevated when an individual has lost an excessive amount of water, such as with sweating, fever, vomiting, and diarrhea. In addition, abnormally high amounts of nonionic urinary constituents, like glucose and protein, increase the urine specific gravity to 1.050 or greater in some individuals suffering from diabetes mellitus or nephrosis. Urine with a fixed low specific gravity of approximately 1.010 that varies little from specimen to specimen is known as isothenuric. This condition is indicative of severe renal damage with disturbance of both the concentrating and diluting abilities of the kidney.

In order to determine if an individual has either an abnormally high or an abnormally low urine specific gravity, and in order to help monitor the course of a medical treatment to determine its effectiveness, simple, accurate and inexpensive specific gravity assays have been developed. In general, the specific gravity of a test sample is a measurement that relates to the density of the test sample. The specific gravity is a value derived from the ratio of the weight of a given volume of a test sample, such as urine, to the weight of the same volume of water under standardized conditions (Eq. 1).

$$Sp.\ Gr. = \frac{\text{weight of urine}}{\text{weight of water}} \qquad \text{Eq. 1}$$

Water has a specific gravity of 1.000. Since urine is a solution of minerals, salts, and organic compounds in water, the specific gravity of urine is greater than 1.000. The relative difference reflects the degree of concentration of the urine specimen and is a measure of the total solids in urine.

Several methods are available to determine the specific gravity of urine. The most widely used method, and possibly the least accurate, employs a urinometer. The urinometer is a weighted, bulb-shaped instrument having a cylindrical stem containing a scale calibrated in specific gravity readings. The urinometer is floated in a cylinder containing the urine sample, and the specific gravity of the urine is determined by the depth the urinometer sinks in the urine sample. The specific gravity value is read directly from the urinometer scale at the junction of the urine with the air. The urinometer method is cumbersome and suffers from the disadvantages of: a) requiring large volumes of urine test sample, b) a difficult and inaccurate reading of the urinometer scale, and c) unreliable assays because the urinometer is not regularly recalibrated.

Refractometry provides an indirect method of measuring the specific gravity of urine. The refractive index of urine is directly related to the number of dissolved particles in urine and, therefore, is directly related to the specific gravity of urine. Consequently, measurement of the refractive index of urine can be correlated to the specific gravity of urine. The refractometer method of determining urine specific gravity is desirable because specific gravity measurements are performed on as little as one drop of urine. However, the refractometer has the disadvantages of requiring daily calibration and not being amenable to home assays.

The falling drop method is another method of assaying for specific gravity which, like the urinometer, directly measures urine specific gravity. In this method, a drop of urine is introduced into each of a series of columns filled with solvent mixtures of increasing and known specific gravity. When the drop of urine comes to rest after its initial momentum has dissipated, and then neither rises nor falls, the specific gravity of the urine is determined to be identical to the specific gravity of the solvent mixture of that particular column. The falling drop method, however, is not widely used in routine urinalysis because of the lengthy time requirements in setting up such a assay and the inability of an individual to perform the assay at home.

The falling drop method described above also can be performed instrumentally. The instrument-based assay uses a specially designed column filled with a silicone oil having a controlled specific gravity and viscosity. The column is designed to measure the time required for a precisely measured drop of test sample to fall a distance defined by two optical gates (lamp-phototransistor pairs) mounted one above the other in a temperature-controlled column filled with a water-immiscible silicone oil of a slightly lower density than the test sample. The falling time is measured electronically and computed into specific gravity units. This specific gravity method is very precise, but the cost of the assay instrument and the degree of skill required to operate the instrument makes home testing for urine specific gravity impractical.

Not one of the above-described specific gravity assay methods is suited to performing specific gravity assays outside a medical office or laboratory. Consequently, reagent impregnated test strips were developed to enable an individual to perform specific gravity assays at home. In general, the test strip assay developed for specific gravity determinations is an indirect assay method, wherein the test strip changes color in response to the ionic strength of the urine sample. The ionic strength of a test sample is a measure of the type and amount of ions present in a test sample. The specific gravity of a test sample is proportional to test sample ionic strength. Therefore, by assaying for the ionic strength of a test sample, the specific gravity is determined indirectly by correlating the ionic strength of the test sample to the specific gravity of the test sample.

The present day specific gravity test strips are pH dependent, and comprise a carrier matrix impregnated with a reagent composition including a polyelectrolyte, such as a partially neutralized poly(methyl vinyl ether/maleic acid); a chromogenic indicator, such as bromothymol blue; and suitable buffering agents. The reagent composition is sensitive to the number of ions, or electrolytes, in the test sample, such that the polyelectrolyte of the reagent composition undergoes an ion exchange, and releases hydrogen ions into the test sample solution in exchange for cations present in the test sample in an amount relative to the ionic strength of the urine sample.

Therefore, as the concentration of electrolytes in urine increases (high specific gravity), more cations are available to exchange with hydrogen ions present on the polyelectrolyte of the reagent composition. The overall result is a release of hydrogen ions into the urine sample, and a resulting pH decrease of the urine sample that causes a color transition of the bromothymol blue chromogenic indicator from blue-green to green to yellow-green in response to increased specific gravity. The resulting color transition, indicating a pH change caused by increasing ionic strength, i.e., increasing specific gravity, is empirically related to the specific gravity of the urine sample.

For test strips utilizing the partially neutralized poly(methyl vinyl ether/maleic acid) polyelectrolyte and bromothymol blue indicator, assays for specific gravity are performed on aqueous test samples having a specific gravity of about 1.000 to about 1.030. A reading of 1.000, or a blue-green color, indicates that the urine has a very low specific gravity, as demonstrated by the lack of a color transition of the chromogenic indicator dye. A specific gravity reading of about 1.005 to about 1.030 is signified by color transitions, from blue-green through green to yellow-green, that serve as reliable indicators of increasing specific gravity.

In accordance with the present day reagent strip method, an individual can readily determine, visually, the specific gravity of a urine sample in the range of about 1.000 to about 1.030. However, the presently available commercial test strips use a pH indicator and are pH dependent. Accordingly, the assay is partially affected by the pH of the urine sample. Therefore, it is desirable to provide a method of determining urine specific gravity that is essentially independent of urine sample pH, such that an accurate specific gravity assay can be interpreted in conjunction with assays for other urine analytes to provide a reliable diagnosis and to allow initiation of a correct medical treatment.

It would be extremely advantageous to have a simple and trustworthy method of assaying for urine specific gravity that allows visual differentiation of specific gravity values from about 1.000 to about 1.035. By providing a semiquantitative method of determining urine specific gravity in an easy to use form, such as a dip-and-read test strip, the urine assay can be performed by laboratory personnel to afford immediate test results. The semiquantitative specific gravity assay results can be interpreted in conjunction with assays for other urine constituents, such that a diagnosis can be made without having to wait for assay results and a medical treatment can be commenced immediately. Furthermore, the test strip method can be performed by an individual at home to semiquantitatively determine the specific gravity of the urine and therefore to help monitor the success of the medical treatment the individual is undergoing.

As will be described more fully hereinafter, the method of the present invention is essentially independent of test sample pH and allows the fast, semiquantitative assay for specific gravity of urine and other aqueous test samples by utilizing a reagent composition comprising a complexing agent, like a polyelectrolyte, an ion exchange material, a chelating agent, or a mixture thereof; a polyvalent metal ion having a valence of at least two; and an indicator capable of interacting with the polyvalent metal ion to provide a color transition. The reagent composition provides sufficient sensitivity and sufficient visual color differentiation between urine samples to yield semiquantitative specific gravity assays. In addition, urine specific gravities of about 1.000 to about 1.035 can be determined quickly.

Any method of assaying for the specific gravity of urine or other aqueous test samples must yield trustworthy and reproducible results by utilizing a reagent composition that undergoes a color transition in response to the specific gravity of the test sample, and not as a result of a competing chemical or physical interaction, such as a pH change or preferential interaction with another test sample component, like protein or glucose. Additionally, the method and composition utilized in the specific gravity assay should not adversely affect or interfere with other test reagent pads that are present on multiple test pad strips.

In accordance with the present invention, the reagent composition can be incorporated into the carrier matrix to provide sufficient sensitivity and color differentiation to assay for cation concentration, and therefore for specific gravity between about 1.000 to about 1.035. In addition, although dry phase test strips have been used to assay for specific gravity, no dry phase test strip has incorporated a complexing agent, a polyvalent metal ion, and an indicator capable of interacting with the polyvalent metal ion to provide a color transition in a semiquantitative assay for specific gravity of a test sample.

Prior patents disclose the polyelectrolyte. dye ion exchange chemistry essentially utilized in the specific gravity assay of urine. For example, Falb et al. U.S. Pat. No. 4,318,709 and Stiso et al. U.S. Pat. No. 4,376,827 disclose a polyelectrolyte-dye technique used to assay for urine specific gravity. Each patent teaches utilizing polyelectrolyte-dye chemistry to determine the specific gravity of urine by monitoring the color transition of the dye.

The Falb et al. and Stiso et al. patents each disclose a composition and a method wherein the cations present in the test sample induce an ion exchange with the polyelectrolyte, thereby introducing hydrogen ions into the test solution. The change in hydrogen ion concentration, i.e., pH, is detected by a pH indicator. Accordingly, the previously disclosed methods are sensitive to the pH of the aqueous solution.

The composition and method of the present invention differ from the above disclosures in that a polyvalent metal ion having a valence of at least two first complexes with a complexing agent, like a polyelectrolyte, to form a polyvalent metal ion complex. Then, as a result of contact between the present reagent composition and a test sample including a sufficient concentration of cations, the cations compete with the polyvalent metal ion for the complexing agent and displace a number of the polyvalent metal ions from the complexing agent. The number of polyvalent metal ions displaced from the complexing agent is directly proportional to the concentration of cations in the test sample.

After being displaced from the complexing agent, the polyvalent metal ions are available to interact with the indicator and form a polyvalent metal ion-indicator complex. The polyvalent metal ion-indicator complex is different in color from the reagent composition and test sample, and therefore provides a detectable and measurable color transition. The color transition can be correlated to the specific gravity of the test sample because the color transition is directly proportional to the amount of polyvalent metal ion released from the complexing agent, which in turn is directly proportional to the cation concentration of the test sample. The cation concentration of the test sample is directly proportional to test sample specific gravity. Accordingly, and in contrast to the Falb et al. and Stiso et al. disclosures, the present method is essentially independent of test sample pH because the color transition results from a pH-independent displacement of polyvalent metal ions, such as ferrous ions or cobaltous ions, from a complexing agent, such as a polyelectrolyte, an ion exchange material or a chelating agent.

The present invention provides a composition and method for semiquantitatively determining the specific gravity of urine and other aqueous test samples by utilizing a reagent composition including an indicator capable of forming a complex with the polyvalent metal ion and providing a color transition. European Patent Application 0 349 934 discloses a test strip and method of determining specific gravity of a sample utilizing a composition including a buffer, a complex former and a pH indicator dye. The complex former can be a crown ether, a cryptand, a podand or a multifunctional ligand. The method disclosed in the European Application is pH dependent, and utilizes a standard pH indicator dye, such as bromothymol blue or thymol blue. European Patent Application 0 349 934 does not teach or suggest a combination of a complexing agent, a polyvalent metal ion and an indicator, as utilized in the present invention, to provide an essentially pH independent assay for specific gravity.

In contrast to the above-described patents, and in contrast to the presently available commercial test strips, the method of the present invention provides a semiquantitative measurement of test sample specific gravity by utilizing a reagent composition including a complexing agent, like a polyelectrolyte, an ion exchange material, a chelating agent, or a mixture thereof; a polyvalent metal ion having a valence of at least two; and an indicator capable of interacting with the polyvalent metal ion to provide a color transition, wherein the method is essentially independent of test sample pH. The present reagent composition undergoes a sufficient color transition upon contact with a test sample to provide a semiquantitative specific gravity assay for liquids having a specific gravity of about 1.000 to about 1.035. Hence, new and unexpected results are achieved in the wet phase and the dry phase reagent strip assay of urine and other aqueous test samples for specific gravity.

SUMMARY OF THE INVENTION

In brief, the present invention is directed to a method and composition for semiquantitatively determining the specific gravity of an aqueous test sample, and especially the specific gravity of a biological fluid, such as urine, perspiration, blood plasma or blood serum. The method utilizes a reagent composition capable of interacting with a test sample to produce a detectable and measurable response that can be correlated to the specific gravity of the test sample. The response is essentially independent of the pH of the test sample. For home use, the reagent composition produces a visually detectable response. For laboratory use, the reagent composition produces a response that is detectable visually or instrumentally.

The method is suitable for wet phase assays and for dry phase assays. In a dry phase assay, the reagent composition is incorporated into a carrier matrix to provide a test pad of a test device. The carrier matrix of the test pad comprises a bibulous porous material, like filter paper, or a nonbibulous porous material, like a glass fiber or a permeable layer of a polymeric material. The reagent composition is homogeneously incorporated into the carrier matrix, and the carrier matrix then holds the reagent composition homogeneously throughout the carrier matrix in a known concentration while maintaining carrier matrix penetrability for the liquid test sample.

More particularly, the present invention is directed to a method of semiquantitatively assaying for the specific gravity of urine and other biological or aqueous test samples by utilizing a new reagent composition. It has been demonstrated a reagent composition including: 1) a complexing agent, 2) a polyvalent metal ion, and 3) an indicator capable of interacting with the polyvalent metal ion to provide a color transition affords sufficient sensitivity to test sample specific gravity, and a sufficient color differentiation between test samples of different specific gravity. In accordance with an important feature of the present invention, the specific gravity of urine and other aqueous test samples can be determined, semiquantitatively, between about 1.000 and about 1.035, and especially between about 1.005 and about 1.030.

Surprisingly, the present method does not rely upon a pH change to provide the color transition and is essentially independent of test sample pH. However, a buffer optionally can be included in the reagent composition to achieve a more spectacular color transition, and accordingly a more accurate measurement of the specific gravity of the test sample. The buffer can be included in the reagent composition to maintain the reagent composition within a pH range that provides the most spectacular and differentiable color transition. Accordingly, an improved assay sensitivity to specific gravity is achieved.

Therefore, one aspect of the present invention is to provide a method and composition for semiquantitatively determining the specific gravity of an aqueous liquid. The composition interacts with cations present in the aqueous test sample to produce a visible change, such as a change in color of a test device, that is indicative of the specific gravity of the test sample.

Another aspect of the present invention is to provide a method of assaying urine or other aqueous test samples, said method having sufficient sensitivity and sufficient visual color resolution to allow differentiation between, and the semiquantitative measurement of, test sample specific gravities.

Another aspect of the present invention is to provide a method of assaying urine or other aqueous test samples utilizing a reagent composition capable of interacting with cations present in urine or other aqueous test samples, and undergoing a detectable and measurable color transition, independent of test sample pH, to establish the specific gravity of the test sample.

Another aspect of the present invention is to provide a reagent composition that interacts with cations present in the test sample and undergoes a visually or instrumentally differentiable color transition to allow the determination of test sample specific gravity of about 1.000 to about 1.035, and especially about 1.005 to about 1.030.

Another aspect of the present invention is to provide a method of assaying for the specific gravity of a liquid test sample by incorporating a reagent composition into a dry phase detection device, wherein the reagent composition comprises: (a) a complexing agent, like a polyelectrolyte, an ion exchange material, a chelating agent or a combination thereof; (b) a polyvalent metal ion having a valence of at least two, like ferrous ion or cobaltous ion; (c) an indicator capable of interacting with the polyvalent metal ion to provide a color transition; and (d) a suitable carrier. Optionally, the reagent composition can include (e) a buffer.

Still another aspect of the present invention is to provide a new and improved method of assaying for the cation concentration or the specific gravity of an aqueous test sample by utilizing a test device including a carrier matrix, said carrier matrix comprising a bibulous matrix, like filter paper, or a nonbibulous matrix, like a glass fiber or a layer of a permeable polymeric material, and said carrier matrix having incorporated therein a reagent composition capable of interacting with cations present in the test sample to provide a color transition.

A further aspect of the present invention is to provide an improved dry phase test strip that incorporates a reagent composition comprising a complexing agent, a polyvalent metal ion and a suitable indicator into the carrier matrix, and thereby provide a pH independent semiquantitative assay for the specific gravity of a test sample.

The above and other aspects and advantages and novel features of the present invention will become apparent from the following detailed description of the preferred embodiments.

DETAILED DESCRIPTION OF THE PREFERRED EMBODIMENTS

In accordance with the method of the present invention, the semiquantitative assay of aqueous test samples for specific gravity is accomplished by utilizing a reagent composition that includes a complexing agent; a polyvalent metal ion; and an indicator capable of interacting with the polyvalent metal ion to provide a color transition. By employing a reagent composition of the present invention, sufficient sensitivity and sufficient visual color differentiation between test samples of differing specific gravities is achieved. Surprisingly, the method does not rely upon a pH change to provide a color transition, and therefore the reagent composition can be buffered to an appropriate pH range for maximum color transition.

The method and composition of the present invention is especially useful in urine assays. In accordance with the method and composition of the present invention, urine specific gravities between about 1.000 and about 1.035, and especially between 1.005 and 1.030, can be differentiated and measured semiquantitatively. Furthermore, the method and composition of the present invention also can be used to determine the specific gravity of blood plasma and serum; and more generally, the specific gravity of many other physiological fluids, like perspiration, as well.

Differentiating between specific gravities is clinically important because urine specific gravities that are either above or below the normal specific gravity range of about 1.010 to about 1.025 for a healthy individual may indicate a potential renal deficiency. A semiquantitative urine specific gravity assay interpreted in conjunction with assays for other urine analytes can assist in diagnosing a diseased state. It should be noted that in regard to urine specific gravities within the relatively normal range of about 1.010 to about 1.025, the method of the present invention still affords color differentiation and sensitivity to urine specific gravity. Clinical benefits are realized in this normal specific gravity range by interpreting the specific gravity assay in conjunction with urine assays for other analytes, such that all of the assays can provide information concerning an abnormal physiological state that must be investigated further.

To achieve the full advantage of the present invention, the method and composition are employed in dry phase, test pad assays to determine the specific gravity of urine or other aqueous test samples. A dry phase test strip, including a test pad comprising a carrier matrix incorporating a reagent composition of the present invention, allows the rapid semiquantitative assay of urine specific gravity by visual means. The method and composition of the present invention also are useful in wet phase assays.

In particular, the present invention allows determination of the specific gravity of a test sample by the visual color change of a test pad on a test strip or by the visual color change of an aqueous solution. Test sample specific gravity is determined by correlating the cation concentration of the test sample to test sample specific gravity. The test strip includes a test pad comprising an inert carrier matrix incorporating a reagent composition comprising a sufficient amount of a complexing agent, a polyvalent metal ion, and an indicator capable of interacting with the polyvalent metal ion to provide a color transition.

The present composition and method allow the rapid colorimetric determination of the specific gravity of a test sample. Previous specific gravity assay methods employed indicator dyes that are sensitive to solution pH. The present method is essentially independent of the pH normally encountered in urine samples, e.g., pH of about 3 to about 9.

The pH indicator dyes conventionally used in specific gravity assays undergo color transitions due to a pH change in the solution resulting from an ion exchange between a polyelectrolyte and cations present in the test sample. The phenomena is fully described in Falb et al. U.S. Pat. No. 4,318,709 and Stiso et al. U.S. Pat. No. 4,376,827, wherein the various dyes, the polyelectrolytes and the buffers required to observe the pH change are disclosed. The Falb et al. and Stiso et al. patents basically describe the present day dry phase test strips employed to assay for urine specific gravity. These present day test strips generally include: (a) an indicator dye that normally undergoes a color transition in the neutral pH range of about 6 to about 8, such as bromothymol blue; (b) a partially neutralized polyelectrolyte; and (c) a buffer.

In accordance with the methods of Stiso et al. and Falb et al., as the ionic strength of the urine increases, hydrogen ions are released into the solution due to an ion exchange between the cations in the test sample and the polyelectrolyte. The overall result is a drop in pH of the solution, and the bromothymol blue indicator changes color from blue-green to green to yellow-green in response to the pH change caused by increasing ionic strength. The increase in ionic strength of an aqueous test sample is directly related to an increase in specific gravity; the color transition of the dye therefore is empirically related to specific gravity values. The present day method suffers from the disadvantage of color transition instability, wherein the color transition fades over a time period of minutes. Accordingly, the accuracy of the results are technique dependent.

The methods disclosed by Stiso et al. and Falb et al. also are sensitive to normal fluctuations in test strip manufacturing. For example, variations in carrier materials and in drying conditions of the test strip, and lot-to-lot differences in a complexing agent, each can influence the final surface pH of the test strip. Variances in the final surface pH of the test strip result in less accurate specific gravity measurements because the test strip becomes either more or less sensitive to pH changes.

In accordance with the present method, assays for the specific gravity of an aqueous test sample are determined by examining a solution or a dry phase test strip for a visual color change after the test sample contacts a solution or a test strip incorporating the reagent composition. The test strip comprises a test pad, said test pad including a carrier matrix incorporating a reagent composition comprising a complexing agent, a polyvalent metal ion, and a suitable indicator. In contrast to previous methods which utilized pH sensitive dyes, the present method is essentially independent of normally-encountered pH values and the reagent composition ca be buffered to provide a pH range that yields the most spectacular color transition.

The present invention differs from the methods disclosed by Stiso et al. and Falb et al. in that the present method does not rely upon a pH change to provide a color transition. Furthermore, the reagent composition can be buffered to a pH that provides the most spectacular color transition. This pH independence eliminates the need for specific gravity corrections of urine samples having a high pH. The present pH independent method also avoids the above-described manufacturing problems associated with the present pH-dependent test strips.

In accordance with an important feature of the present invention, the cation concentration of urine can be correlated to urine specific gravity. Therefore, measuring urine cation concentration provides an indirect method of measuring urine specific gravity. In accordance with the present invention, urine specific gravity is determined from the color transition resulting from the formation of polyvalent metal ion-indicator complexes. In the present method, a polyvalent metal ion, such as ferric ion, first is bound sufficiently strongly to a complexing agent such that no color transition occurs when an indicator is added to the polyvalent metal ion complex. Then, in the presence of a sufficient concentration of urinary cations, the polyvalent metal ion first is displaced from the complexing agent, then interacts with the indicator to form a polyvalent metal ion-indicator complex, and a color transition results.

More particularly, the ability of a complexing agent and a polyvalent metal ion to interact and form a complex is influenced by the cation concentration of a solution, with the ability of the complexing agent and the polyvalent metal ion to form a complex decreasing as cation concentration increases. The present method utilizes this property in a pH independent method and device to assay an aqueous test sample for specific gravity.

Cations in solution affect the ability of the polyvalent metal ion to complex with the complexing agent because the cations successfully compete with the polyvalent metal ion with regard to complexing with the complexing agent. Therefore, as the cation concentration of a solution increases (i.e., specific gravity increases), a greater amount of the polyvalent metal ion is displaced from the complexing agent because a portion of the cations in solution preferentially complex with the complexing agent at the expense of the polyvalent metal ion. The displacement of polyvalent metal ions from the complexing agent results in a color transition because the polyvalent metal ion then is available to interact with the indicator to form a polyvalent metal ion-indicator complex having a color different from the color of the polyvalent metal ion-complexing agent complex. Therefore, the amount of polyvalent metal ion displaced from the complexing agent, as determined by the color transition, can be correlated to the cation concentration of the test sample, and, in turn, to test sample specific gravity.

The method of the present invention utilizes a color transition resulting from cations in the test sample displacing polyvalent metal ions complexed with a complexing agent. The polyvalent metal ions then are available to interact with an indicator to provide the color transition. The reagent composition allows the semiquantitative specific gravity measurement of a test liquid having a specific gravity of about 1.000 to about 1.035. In accordance with an important feature of the present invention, the displacement of polyvalent metal ions from the complexing agent, and the subsequent interaction between the polyvalent metal ions and the indicator, provides a differentiable color transition that can be correlated to the specific gravity of a test sample. Measurement of test sample specific gravity is achieved because a sufficient color resolution exists between test samples of different specific gravity.

Therefore, the reagent composition of the present invention comprises: (a) a complexing agent; (b) a polyvalent metal ion; (c) an indicator capable of interacting with the polyvalent metal ion to provide a color transition; and (d) a suitable carrier. The reagent composition is used in a method, such as in a wet phase method or in a dry phase test strip method, to semiquantitatively assay a test sample, like urine, for cation concentration or for specific gravity.

The complexing agent can be a polyelectrolyte, an ion exchange material, a chelating agent, essentially any other compound capable of interacting with a polyvalent metal ion or a combination thereof. The complexing agent is capable of interacting, or binding, sufficiently strongly with a polyvalent metal ion such that no color transition occurs in the presence of an indicator. The complexing agent also is capable of releasing at least a portion of the polyvalent metal ions when a sufficient amount of monovalent or divalent metal ions, or a mixture thereof, is added to a solution of the polyvalent metal ion and the complexing agent. Therefore, when metal ions are introduced into a medium that includes polyvalent metal ions complexed to a complexing agent, polyvalent metal ions are displaced from the complexing agent, and are available to interact with the indicator and cause the medium to undergo a color transition. The color transition is proportional to the amount of polyvalent metal ions released from the complexing agent; which in turn is related to the amount of monovalent and divalent metal ions added to the medium.

In general, the complexing agent can be any compound capable of complexing with a polyvalent metal ion. Accordingly, the complexing agent usually includes sites having either a partial or a full negative charge. The particular complexing agent included in the reagent composition can be determined by a person skilled in the art in designing test kits to provide a specific gravity assay having maximum visual color resolution and maximum sensitivity.

The complexing agent can be selected from a wide variety of classes of compounds, and the amount of complexing agent in the reagent composition can vary greatly. However, a sufficient amount of complexing agent is included in the reagent composition to complex with essentially all of the polyvalent metal ions included in the reagent composition. The complexing agent generally is present in the reagent composition in a concentration of about 0.04 mM (millimolar or millimoles per liter) to about 0.2 mM, and preferably from about 0.05 mM to about 0.1 mM. To achieve the full advantage of the present invention, the complexing agent is present in the reagent composition in a concentration of about 0.05 mM to about 0.08 mM.

One particular class of useful complexing agents is the polyelectrolytes, wherein the polyelectrolyte has a sufficient number of negatively-charged sites to complex with the polyvalent metal ions present in the reagent composition. Preferably, the polyelectrolyte is a strong polyelectrolyte, such as for example, but not limited to, a poly(vinyl sulfate); a poly(vinyl sulfonate); a poly(styrenesulfonate); a maleic acid-methyl vinyl ether copolymer; polyvinylpyrrolidone; polyethylenimine; polymeric secondary amines; polymeric tertiary amines; a polypeptide including cysteine, glycine, histidine, leucine or isoleucine; and mixtures thereof. Such strong polyelectrolytes ionize essentially completely in aqueous solution, thereby providing a sufficient number of negatively charged sites to complex with a polyvalent metal ion.

The complexing agent also can be an ion exchange material, such as for example, but not limited to, cellulose phosphate, carboxymethylcellulose, diethylaminoethylcellulose, a paper loaded with a sulfonic acid resin, or a glass fiber including sulfonic acid groups, and combinations thereof. The sulfonic acid resin loaded onto the filter paper is polystyrenesulfonic acid.

The complexing agent also can be a relatively low molecular weight chelating agent, such as, for example, but not limited to, a polycarboxyalkylamine, like ethylenediaminetetraacetic acid, ethylenediaminediacetic acid, N-(2-hydroxyethyl)ethylenediaminetriacetic acid, cyclohexylenediaminetetraacetic acid, nitrilotriacetic acid, iminodiacetic acid, ethylenediaminediacetic dipropionic acid, hydroxyethyliminodiacetic acid, diethylenetriaminepentaacetic acid, ethylenebis(oxyethylenenitrilo)tetraacetic acid, or N-(2-acetamido)iminodiacetic acid; aminotris(methylene phosphoric acid); hydroxyethylidene diphosphoric acid; hexamethylenediaminetetra(methylene phosphonate); nitrilopropionic acid; 1-hydroxyethane-diphosphonic acid; a polycarboxylic acid or salt, like malonic acid, citric acid, oxalic acid, tartaric acid or gluconic acid; a polyhydroxy compound, like sorbitol; a lignosulfonate; a glucoheptonate; dimethylglyoxime; salicylate complexes, like bissalicylaldehydeethylenediimine; ethylenediamine; histidine; proline or a proline derivative; phenylalanine; benzoyltrifluoroacetone; thenoyl-trifluoracetone; dithionate derivatives; polyethyleneamines, like triethyleneamine; a 2,4-pentanedione derivative; a dipyridine derivative; triethylanepyridine amine; a thiocrown ether, like 1,4,8,11,22,25-octathiacyclooctasane; a triphenylphosphine; or mixtures thereof. Other useful complexing agents are disclosed in A.E. Martell et al., *Chemistry of the Metal Chelate Compounds*, (1952), Appendix 1, page 514 et seq., incorporated herein by reference.

In addition to the complexing agent, the reagent composition also includes a metal ion having a valence of at least two, i.e., a polyvalent metal ion. The polyvalent metal ion is present in a sufficient amount such that essentially all of the polyvalent metal ion is complexed with the complexing agent. Then, as a result of displacement from the complexing agent, the polyvalent metal ion is available to interact with the indicator to provide a detectable and differentiable color transition.

The particular amount of polyvalent metal ion included in the reagent composition can be determined by a person skilled in the art of designing test kits after considering the particular complexing agent, the amount of complexing agent included in the reagent composition, the particular polyvalent metal ion and the particular indicator included in the reagent composition in order to provide a maximum color transition. Generally, however, the polyvalent metal ion is present in the reagent composition in an amount of about 0.02 mM to about 5 mM, and preferably about 0.05 mM to about 3 mM.

In accordance with an important feature of the present invention, it is envisioned that essentially any polyvalent metal ion: 1) capable of complexing with the complexing agent, and 2) undergoing a color transition in the presence of the indicator after displacement from the complexing agent, can be included in the reagent composition of the present invention. Accordingly, a polyvalent metal ion useful in the reagent composition is, for example, but not limited to, ferric ion, ferrous ion, calcium ion, magnesium ion, cobalt(II) ion, cobalt(III) ion, cupric ion, mercuric ion, stannic ion, nickel(II) ion, lead(II) ion, manganese(III) ion, cadmium(II) ion, zinc(II) ion, molybdenum(V) ion, chromium(IV) ion and vanadium(III) ion, or mixtures thereof. In addition, other polyvalent metal ions also can be used as long as the polyvalent metal ion can be complexed sufficiently strongly to the complexing agent to prevent a premature color transition upon contact with the indicator. To achieve the full advantage of the present invention, the polyvalent metal ion is ferric ion, cobaltous ion, ferrous ion, magnesium ion, or a mixture thereof. The polyvalent metal ion is included in the reagent composition in the form of a water soluble salt, wherein the anion does not interfere with the specific gravity assay. Typically, the polyvalent metal ion is included in the reagent composition as a metal chloride salt.

In addition to the complexing agent and the polyvalent metal ion, the reagent composition also includes an indicator capable of interacting with the polyvalent metal ion to provide a color transition. After displacement from the complexing agent due to the presence of cations in the test sample, the polyvalent metal ion is available to interact with the indicator to cause a color transition. The color transition can be either an increase or a decrease in color intensity and degree. The color transition usually is an increase in color intensity and degree.

Therefore, a solution including a polyvalent metal ion complexed to a complexing agent undergoes a color change in the presence of an indicator when polyvalent metal ions are displaced from the complexing agent. Monovalent cations, like sodium and potassium, are the predominant cations in test samples like urine. However, relatively high concentrations of divalent cations, like calcium and magnesium, also are present in urine. The monovalent and divalent cations displace polyvalent metal ions bound to the complexing agent because the monovalent and divalent cations successfully compete with the polyvalent metal ions for the available negatively charged sites on the complexing agents.

In general, the indicator can be essentially any compound, such as a dye, that interacts with the displaced polyvalent metal ion in the reagent composition to undergo a color transition. Such indicators undergo a color transition in response to a displacement of polyvalent metal ions from the complexing agent. The polyvalent metal ions are displaced from the complexing agent by cations, like sodium or magnesium, present in the test sample. The degree and intensity of the color transition are directly related to the concentration of monovalent and divalent cations in the test sample; and the concentration of the cations in the test sample is directly related to the specific gravity of the test sample. Therefore, the degree and intensity of the color transition are correlated to the specific gravity of the test sample.

The particular indicator included in the reagent composition can be determined by those skilled in the art of designing test kits after considering the particular polyvalent metal ion included in the reagent composition in order to provide a specific gravity assay having maximum visual color resolution and maximum sensitivity. The indicator generally is present in the reagent composition in a concentration of about 0.02 mM to about 4 mM, and preferably about 0.04 mM to about 3 mM. To achieve the full advantage of the present invention, the indicator is present in the reagent composition at a concentration of about 0.1 mM to about 2 mM.

Several indicators useful in the method of the present invention are well known dyes that presently are available commercially. Examples of indicators that bind to a polyvalent metal ion and undergo a color change include, but are not limited to, 1,10-phenanthroline, bathophenanthroline, 2,2'-dipyridyl, tripyridyl-s-triazine, Tiron ® (disodium pyrocatechol-3,5-disulfonate), dimethylglyoxime, rubeanic acid, eriochrome black T, rhodizonic acid, calmagite, gallocyanine, diphenylthiocarbazone, diphenylcarbazone, potassium ferricyanide, pyrocatechol violet, 5-methyl-1,10-phenanthroline, 5-nitro-1,10-phenanthroline, 3-(4-phenyl-2-pyridyl)-5,6-diphenyl-1,2,4-triazine, 3 (4-phenyl-2-pyridyl)-5,6-diphenyl-1,2,4-triazinetrisulfonic acid trisodium salt, 3 (2 pyridyl)-5,6-diphenyl 1,2,4-triazine, 3-(2-pyridyl)-5,6-diphenyl-1,2,4 triazinedisulfonic acid disodium salt, phenyl-2-pyridyl ketoxime, 4'-phenyl-2,2'2''-terpyridine, 2,2',2''-terpyridine, 4,4',4''-triphenyl-2,2',2''-terpyridine, 2,3,5,6-tetrakis(2'-pyridyl)pyrazine, 2,2,-biquinoline, bis-cyclohexanone oxaldihydrazone, 2,4-bis(5,6-diphenyl-1,2,4-triazin-3-yl)pyridine, 2,4-bis(5,6 diphenyl-1,2,4-triazin-3yl)pyridinetetra-sulfonic acid tetrasodium salt, 4,4'-dihydroxy-2,2'-biquinoline, 4,7-dihydroxy-1,0-phenanthroline, 4,4'-dimethyl-2,2'-bipyridine, 2,9-dimethyl-1,10-phenanthroline, 2,9 dimethyl-4,7-diphenyl-1,10-phenanthroline, 2,9-dimethyl-4,7-diphenyl-1,10-phenanthrolinedisulfonic acid, 4,7-dimethyl-1,10-phenanthroline, 5,6-dimethyl-1,10-phenanthroline, and mixtures thereof.

Such indicators exhibit an excellent ability to bind to a polyvalent metal ion and undergo a detectable and differentiable color transition that can be correlated to the specific gravity of a test sample. Other nonlimiting exemplary indicators useful in the reagent composition can be found in the *Handbook of Chemistry and Physics, 71st Edition* (1990–1991) at pages 8–8 through 8–11, incorporated herein by reference.

The present method is performed in a pH range of about 4 to about 9. A specific pH range is selected wherein the indicator undergoes a maximum color change upon interaction with the polyvalent metal ion. The reagent composition, therefore, optionally can include a buffer to maximize the color transition.

If a buffer is included in the reagent composition, any of various types of buffers can be used in the reagent composition of the present invention to provide a desired pH. The buffer optionally is included to maintain the reagent composition at a substantially constant pH to optimize the response of an indicator to the specific gravity of the test sample.

The amount of optional buffer included in the reagent composition depends upon the nature of the polyvalent metal ion and the indicator included in the reagent composition. The concentration of the buffer usually is 0 millimolar (mM) to about 200 mM, and preferably 0 mM to about 100 mM. The particular buffer used in the reagent composition also depends upon, and varies with, the indicator and polyvalent metal ion included in the reagent composition. For optimum assay results, the pH of the reagent composition generally is maintained at a pH value in the range of about 4 to about 9, and preferably in the range of about 5 to about 9. To achieve the full advantage of the present invention, the buffer maintains the pH value of the reagent composition about 6 to about 9.

Exemplary optional buffers include, but are not limited to, acetate; BICINE; phthalate, borate; trichloracetate; sulfosalicylate; phosphate; tartarate; glycine; citrate; succinate; maleic acid; 2,2-bis(hydroxymethyl) 2,2′, 2″-nitrilotriethanol; 3,3-dimethylglutaric acid; 3-N-morpholinopropanesulfonic acid (MOPS); malonic acid; 1,3bis[tris(hydroxymethyl)methylamino]propane (Bis-TRIS); tris(hydroxymethyl)aminomethane (TRIS); N-(carbamoylmethyl)taurine (ACES); tris(hydroxymethyl)aminomethane-maleic acid (TRIS-maleate); tris(-hydroxymethyl)aminomethane-malonic acid (TRIS-malonate); 3-N-(trishydroxymethyl)methylamino-2-hydroxypropanesulfonic acid (TAPSO); 2-([tris(hydroxymethyl)methyl]amino)ethanesulfonic acid (TES); 1,4-piperazinebis(ethanesulfonic acid) (PIPES); 4-morpholinoethanesulfonic acid (MES); N-2-hydroxyethylpiperazine-N′-2-ethanesulfonic acid (HEPES); and other suitable buffers well known in the art, or mixtures thereof.

In addition to the indicator, the polyvalent metal ion and the complexing agent, other optional ingredients, in addition to the buffer, that do not materially alter the nature or the function of the essential ingredients, and that do not interfere with the assay for specific gravity, also can be included in the reagent composition. For example, the reagent composition optionally can include a compound to improve the wetting of the test pad of the test device by the test sample. This compound usually is a nonionic surfactant. An octoxynol, a nonoxynol or an ethoxylated fatty alcohol is the preferred nonionic surfactant. The surfactant is included in the indicator reagent composition in a concentration of 0 mM to about 200 mM, and preferably in a concentration of 0 mM to about 100 mM.

The reagent composition also can include a polymeric material that improves the stability and uniformity of the color transition of the test device. Suitable polymeric materials include, but are not limited to, polyvinyl alcohol, gum arabic, gelatin, align, carrageenan, casein, albumin, methyl cellulose and similar natural and synthetic polymeric materials. The polymeric material generally is included in the reagent composition in an amount of 0% to about 5%, and preferably 0% to about 4%, by total weight of the reagent composition.

In addition, inert background dyes can be included in the reagent composition to improve the color resolution and differentiation of the color transition in the present assay for specific gravity. Suitable background dyes include, but are not limited to, ethyl orange (4-(4-diethylaminophenylazo) benzenesulfonic acid); Orange G (4-(2-hydroxy-(7,9 sodium disulfonate)-1-naphthylazo)-benzene); disperse orange 11, 13, or 25; calcomine orange; methyl orange; and orange II (4-(2-hydroxy-1-naphthylazo) benzenesulfonic acid), or combinations thereof. A background dye is included in the reagent composition of the present invention at a concentration of 0 mM to about 2 mM, and preferably 0 mM to about 1 mM.

The carrier for the ingredients included in the reagent composition is water, a water miscible alcohol or a water-alcohol mixture. Suitable water-miscible alcohols, include, for example, but are not limited to, methanol, ethanol, isopropyl alcohol and combinations thereof. However, because of the limited water or alcohol solubility of particular ingredients included in the indicator reagent composition, other organic solvents such as ethylene glycol, propylene glycol, acetone, dimethylformamide, dimethylsulfoxide, acetonitrile, ethyl acetate and similar solvents can be included in the carrier. The selection of a suitable organic solvent or solvents, in addition to water and alcohols, to include in the carrier of the reagent composition is within the capability of those skilled in the art of designing diagnostic assays. A carrier comprising water and an alcohol, like methanol or ethanol, or water and a water miscible organic solvent, is especially preferred because a carrier matrix impregnated with the reagent composition can be dried within a few to several minutes.

As previously described, the reagent composition undergoes a color transition as a result of contact with a test sample to provide an assay for test sample specific gravity. The intensity and degree of the color transition are used to semiquantitatively determine the specific gravity of the test sample. In accordance with an important feature of the present invention, a reagent composition of the present invention provides a sufficiently resolved and differentiated color transition such that the specific gravity of a test sample can be measured without the use of color-measuring instruments, such as spectrophotometers or colorimeters. However, if desired, such color-measuring instruments can be used to measure the difference in color degree and intensity between the test sample and a solution having a known specific gravity.

The intensity and degree of the color transition are used to determine the specific gravity of the test sample by comparing or correlating the color produced by the test sample to colors produced by solutions having a known specific gravity. In accordance with an important feature of the present invention, the reagent composition provides a sufficiently resolved and differentiated color transition such that the specific gravity of the test sample can be measured for test samples having a specific gravity of about 1.000 to about 1.035 without the use of color-measuring instruments.

Accordingly, the specific gravity assay method of the present invention, utilizing a reagent composition including a complexing agent, a polyvalent metal ion and an indicator capable of interacting with the metal ion to undergo a color transition, provide a reliable semiquantitative specific gravity assay, and also increases physician confidence in the specific gravity assay. In addition, because of the large number of urine assays for specific gravity being performed at home by untrained individuals, as opposed to trained physicians or technicians in the laboratory, it is imperative to provide reliable assay methods for the specific gravity of urine and serum.

To demonstrate the new and unexpected results achieved by the method and composition of the present invention, reagent compositions, including a complexing agent, a polyvalent metal ion and a suitable indicator, were prepared, then used in wet phase assays and in dry phase assays for the specific gravity of a test sample.

EXAMPLE 1

REAGENT COMPOSITION AND EFFECTS OF CATIONS ON THE REAGENT COMPOSITION

An aqueous reagent composition of the present invention including a complexing agent (copolymer of maleic acid and methyl vinyl ether; 0.6% by weight), a polyvalent metal ion (magnesium ion; 0.04 mM) and an indicator (calmagite; 0.04 mM) in deionized water, and buffered to pH 9.0 with glycine, was prepared. The reagent composition was blue in color. An identical reagent composition was prepared except a 340 mM aqueous sodium chloride solution was substituted for the deionized water. The resulting composition was lavender in color showing that sodium ions displace magnesium ions from the complexing agent, and that a subsequent interaction between the magnesium ions and calmagite occurs.

In another experiment, the reagent composition of Example 1 was contacted with standardized solutions including the cations sodium, potassium, calcium and ammonium, and having an increasing specific gravity. The color transitions of the wet phase assays ranged from blue through blue-lavender through lavender to pink-lavender for standardized solutions having a specific gravity of 1.000 through 1.030. In accordance with an important feature of the present invention, the color resolution achieved by using a present reagent composition, e.g., the reagent composition of Example 1, permits the detection and differentiation of test sample specific gravities in the range of about 1.000 to about 1.035.

A reagent composition including a complexing agent, a polyvalent metal ion and an indicator, as described above in Example 1, can be used in dry phase, test pad assays for specific gravity. The dry phase, test pad assay for specific gravity utilizing the reagent composition is performed in accordance with methods well known in the art. In general, the assay for specific gravity is performed by contacting the urine or other test sample with an analyte detection device that includes the reagent composition. The analyte detection device can be dipped into the test sample, or the test sample can be applied to the analyte detection device dropwise. The resulting change in color of the analyte detection device reveals the specific gravity of the test sample; and, if so designed, the resulting color transition can be compared to a standardized color chart to provide a measurement of the specific gravity of the urine or test sample.

Typically, the analyte detection device is a test strip impregnated with a reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test ample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents and does not contaminate the urine or other test samples either by test sample extraction of components comprising the carrier matrix or by appreciably altering the urine or test sample in a way to make the subsequent assays inconclusive, inaccurate or doubtful. The carrier matrix also is porous or absorbent relative to the liquid test sample.

The expression "carrier matrix" refers either to bibulous or nonbibulous matrices that are insoluble in water and other physiological fluids and that maintain their structural integrity when exposed to water and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally-occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate or polystyrene, and the carrier matrix is most advantageously constructed from filter paper or polymeric films.

To achieve the full advantage of the present invention, the reagent composition is incorporated into a suitable carrier matrix to provide a test pad, and the test pad is utilized in a dry phase test strip for the specific gravity assay of an aqueous test sample. The method of the present invention provides an economical, accurate and reliable assay of aqueous test samples that can be performed at home or in the laboratory.

In accordance with the method of the present invention, to perform a dry phase, test strip assay for specific gravity, the reagent composition including a complexing agent, a polyvalent metal ion, and an indicator and a carrier first is prepared. A bibulous matrix, such as filter paper, like WHATMAN CCP500 filter paper, available commercially from Whatman Ltd., Maidstone, Kent, U.K., then is saturated with the reagent composition either by spreading, by immersing or by spraying the reagent composition onto precut strips of the filter paper. After removing the carrier by oven drying in an air oven at about 50° C. for about 15 to 20 minutes, the filter paper incorporating the reagent composition is cut to an appropriate size, such as a pad having dimensions of about 0.25 cm by about 0.25 cm to about 1.0 cm by about 1.0 cm. The filter paper incorporating the reagent composition then is secured to an opaque or transparent hydrophobic plastic handle with double sided adhesive tape.

In another embodiment of the present invention, the complexing agent is an ion exchange material. The ion exchange material can be a filter paper that is loaded with a sulfonic acid resin, such as WHATMAN SA-2 filter paper that is loaded with polystyrenesulfonic acid. In this embodiment, the complexing agent previously has been incorporated into the bibulous matrix, and the bibulous matrix therefore is saturated with a solution, or solutions, including the polyvalent metal ion and the indicator, preferably in a two dip process. The test strip then is dried in the conventional manner.

In either embodiment, the resulting test strip then was dipped into a fresh, uncentrifuged urine sample for a sufficient time to saturate the test pad with the sample. After waiting a predetermined time, such as about 10 seconds to about 60 seconds, the test strip is examined, either visually or instrumentally, for a response. The degree and intensity of the color transition of the test pad reveal the specific gravity of the urine sample.

In accordance with another important feature of the present invention, it is well within the experimental techniques of those skilled in the art of preparing test devices to determine the proper balance between size of test pad; the strength of reagent composition; the identity and amount of the complexing agent, polyvalent metal ion and the indicator in the reagent composition; the amount of test sample; and the method of introducing the test sample to the test strip, such as by pipetting rather than dipping, to provide detectable and differentiable color transitions, such that a comparison, either visually or instrumentally, to color standards derived from solutions of known specific gravity is possible.

In many cases simple visual observation of the test strip provides the desired information. If more accurate information is required, a color chart bearing color spots corresponding to various standard specific gravities can be prepared for the particular reagent composition used in the test strip. The resulting color of the test strip after contact with the urine sample then can be compared with the color spots on the chart to determine the specific gravity of the test sample.

If a still more accurate determination is required, a spectrophotometer or colorimeter can be used to more precisely determine the degree and intensity of the color transition. In addition, the dry phase, reagent strip assay can be made quantitative by employing spectrophotometric or colorimetric techniques, as opposed to visual techniques, in order to more reliably and more accurately measure the degree and intensity of the color transition, and therefore more accurately measure the specific gravity of the test sample.

In accordance with an important feature of the present invention, the reagent composition includes a polyvalent metal ion and an indicator that are capable of interacting to form a complex and provide a color transition. The color transition can be from colorless to a color, from a color to colorless, or from a first color (i.e., the color of the polyvalent metal ion-complexing agent complex) to a second color (i.e., the color of the polyvalent metal ion-indicator complex), as long as the color transition is sufficient for detection and differentiation. Usually, the color transition exhibited between a polyvalent metal ion and an indicator is most spectacular within a particular, and relatively narrow, pH range. Therefore, the reagent composition preferably is buffered within the pH range wherein the color transition is most spectacular. To achieve the full advantage of the present invention, the reagent composition is buffered to a pH of about 6 to about 9. Within this pH range, the color transition is most spectacular and assay errors due to urine pH are essentially eliminated.

The following Table I illustrates various combinations of polyvalent metal ions and indicators, and the color transition resulting from the formation of a complex between the polyvalent metal ion and the indicator. The color transitions illustrated in Table I occurred in the absence of a complexing agent, and are sufficiently differentiable to provide a method of measuring test sample specific gravity.

TABLE I

COLOR TRANSITIONS RESULTING FROM AN INTERACTION BETWEEN A POLYVALENT METAL ION AND AN INDICATOR

| METAL ION | INDICATOR | pH | COLOR TRANSITION[1] |
|---|---|---|---|
| FERROUS[2] | 1,10-PHENANTHROLINE[3] | 5.0–9.0[4] | MOD. ORANGE |
| | BATHOPHENANTHROLINE | 5.0–9.0 | BRIGHT PINK |
| | POTASSIUM FERRICYANIDE | 5.0–6.0 | MOD. BLUE |
| | 2,2'-DIPYRIDYL | 5.0–9.0 | MOD. PINK |
| | TRIPYRIDYL-S-TRIAZINE | 5.0–8.0 | INT. PURPLE |
| FERRIC | TIRON | 5.0 | MOD. BLUE |
| | POTASSIUM FERROCYANIDE | 5.0–7.0, 9.0 | MOD. PURPLE |
| | PYROCATECHOL VIOLET | 5.0 | ORANGE TO PURPLE |
| NICKEL | DIMETHYLGLYOXIME | 8.0 | FAINT PINK |
| | RUBEANIC ACID | 8.0 | MOD. BLUE |
| CALCIUM | ERIOCHROME BLACK T | 1N NaOH | ROSE RED TO PURPLE |
| | SODIUM RHODIZONATE | 1N NaOH | PURPLE |
| MAGNESIUM | ERIOCHROME BLACK T | 8.0, 9.0 | BLUE TO PURPLE |
| | CALMAGITE | 9.0 | BLUE TO LAVENDER-RED |
| COBALTOUS | RUBEANIC ACID | 8.0 | MOD.-INT. YELLOW |
| | GALLOCYANINE | 8.0 | BLUE TO LAVENDER |
| LEAD | GALLOCYANINE | 6.0–8.0 | BLUE TO LAVENDER |
| | DITHIZONE | 5.0–9.0 | YELLOW TO PINK-ORANGE |
| | DIPHENYLCARBAZONE | 7.0–8.0 | MOD.-INT. LAVENDER |

TABLE I-continued
COLOR TRANSITIONS RESULTING FROM AN INTERACTION BETWEEN A POLYVALENT METAL ION AND AN INDICATOR

| METAL ION | INDICATOR | pH | COLOR TRANSITION[1] |
|---|---|---|---|
| MERCURIC | DIPHENYLCARBAZONE | 4.0–8.0 | INT. PURPLE |

[1] Unless otherwise indicated, the color change was from essentially colorless to the listed color, MOD. is moderate, INT. is intense; and
[2] Polyvalent metal ions were present at a concentration of 1.0 mM;
[3] Indicators were present at a concentration of 1.0 mM; and
[4] Combinations were tested at each pH, pH is buffered using the following buffers at 0.5M:
pH 5.0 Acetate
6.0 MES
7.0 ACES
8.0 HEPES
9.0 Glycine.

Various combinations of a polyvalent metal ion and an indicator also were tested in the presence of various complexing agents to determine the response of a reagent composition to sodium and calcium ions. In particular, aqueous solutions including either sodium ions (340 meq/L, milliequivalents per liter) or calcium ions (10 meq/L) were added to various combinations of a complexing agent, an indicator and a polyvalent metal ion. The results are summarized below in Table II. In each experiment, the complexing agent was a polyelectrolyte. Table II illustrates that a reagent composition including magnesium ions, calmagite and either poly(methyl vinyl ether/maleic anhydride) or polystyrenesulfonic acid provided an excellent response to sodium and calcium ions in wet phase assays.

TABLE II
REAGENT COMPOSITION RESPONSES TO SODIUM AND CALCIUM IONS

| POLYVALENT METAL ION-INDICATOR | COMPLEXING AGENT | pH | Na RESPONSE | Ca RESPONSE |
|---|---|---|---|---|
| Ferric-Tiron | GANTREZ AN 119 | 5.0 | Faint | (none) |
| Nickel-Dimethylglyoxime | GANTREZ AN 119 | 8.0 | Faint | (none) |
| Nickel-Dimethylglyoxime | 7374A[2] | 8.0 | Small | (none) |
| Calcium-Calmagite | GANTREZ AN 119 | NaOH | Small | (none) |
| Magnesium-Calmagite | GANTREZ AN 119 | 9.0 | Mod. | Very Fnt. |
| Magnesium-Calmagite | PSS[3] | 9.0 | Mod. | Very Fnt. |
| Magnesium-Calmagite | 7374A | 9.0 | Small | (none) |
| Magnesium-Calmagite | 7376A[4] | 9.0 | Small | (none) |
| Magnesium-Eriochrome Black T | GANTREZ AN 119 | 8.0 | (none) | (none) |
| Magnesium-Eriochrome Black T | GANTREZ AN 119 | 9.0 | Small | (none) |
| Magnesium-Eriochrome Black T | PVP[5] | 8.0 | (none) | (none) |
| Magnesium-Eriochrome Black T | PVP[5] | 9.0 | (none) | (none) |
| Magnesium-Eriochrome Black T | 6235[6] | 8.0 | (none) | (none) |
| Magnesium-Eriochrome Black T | 6235[6] | 9.0 | (none) | (none) |
| Magnesium-Eriochrome Black T | 7374A | 8.0 | Faint | (none) |
| Magnesium-Eriochrome Black T | 7374A | 9.0 | Faint | Very Fnt. |
| Magnesium-Eriochrome Black T | 7376A | 8.0 | Faint | (none) |
| Magnesium-Eriochrome Black T | 7376A | 9.0 | Faint | (none) |
| Cobaltous-Gallocyanine | GANTREZ AN 119 | 8.0 | (none) | (none) |
| Lead-Gallocyanine | GANTREZ AN 119 | 8.0 | (none) | (none) |
| Lead-Gallocyanine | PVP | 8.0 | Faint | (none) |

[1] GANTREZ AN 119 is a poly(methyl vinyl ether/maleic anhydride) available commercially from GAF Corporation, Wayne, N.J.;
[2] 7374A is a cationic poly(dimethylaminopropylacrylamide), provided by Bayer AG, Leuerkeusen, Germany;
[3] PSS is polystyrenesulfonic acid;
[4] 7376A is a cationic poly(trimethylammoniumpropylmethacrylamide), provided by Bayer AG, Leuerkeusen, Germany;
[5] PVP is polyvinylpyrrolidone available commercially from GAF Corporation, Wayne, N.J., and;
[6] 6235 is a cationic linear poly-N-methylvinylamine hydrochloride, provided by Bayer AG, Leuerkeusen, Germany.

In another reset of experiments, various chelating agents were utilized as the complexing agent. These experiments illustrated the relationship between the binding constant of the polyvalent metal ion to the chelating agent and the displacement of the polyvalent metal ion from the chelating agent by sodium, calcium or magnesium ions. In each experiment illustrated in Table III, the indicator is gallocyanine and the polyvalent metal ion is cobalt(II) (cobaltous).

TABLE III

RESPONSE OF COBALTOUS ION, GALLOCYANINE AND A CHELATING AGENT TO SODIUM, CALCIUM AND MAGNESIUM IONS

| CHELATING AGENT | pK (COBALTOUS) | COLOR | RESPONSE Na | Ca | Mg |
|---|---|---|---|---|---|
| CONTROL no cobalt(II) | — | BLUE | — | — | — |
| CONTROL with cobalt(II) | — | LAVENDER | — | — | — |
| MALONIC ACID | 3.7 | LAVENDER | — | — | — |
| ETHYLENEDIAMINE | 5.9 | LAVENDER | — | — | — |
| HISTIDINE | 7.3 | BLUE | NONE | SLIGHT | SMALL |
| PHENYLALANINE | 7.9 | LAVENDER | — | — | — |
| PROLINE | 9.3 | LAVENDER | — | — | — |
| BTFA[1] | 10.5 | BLUE | NONE | SLIGHT | LARGE |
| TTFA[2] | 10 | BLUE | SLIGHT | SMALL | LARGE |
| EDDA[3] | 11.0 | BLUE | NONE | SLIGHT | MODERATE |
| EDTA[4] | 16.0 | BLUE | NONE | NONE | SLIGHT |

[1] BTFA is benzoyltrifluoroacetone (10 mM);
[2] TTFA is thenoyltrifluoroacetone (10 mM);
[3] EDDA is ethylenediaminediacetic acid (10 mM); and
[4] EDTA is ethylenediaminetetraacetic acid (10 mM).

The binding constants (pK) of cobalt(II) ion with various chelating agent are listed in Table IV in ascending order. The binding constants were listed in A.E. Martell and M. Calvin, *Chemistry of Metal Chelate Compounds*, Prentice Hall (1952), Appendix I at page 514 et seq. Gallocyanine, in the absence of cobalt(II) ion, exhibits a moderate blue color at pH 8.0. The gallocyanine and cobalt(II) ion complex at pH 8.0 is lavender in color.

A chelating agent that binds cobalt(II) ion sufficiently strongly provides a blue solution in the presence of gallocyanine because no free cobalt(II) ion is available to interact with the gallocyanine. Displacement of cobalt(II) ion from the chelating agent by various cations, e.g., sodium, calcium or magnesium, in the presence of gallocyanine, results in a color change from blue to lavender.

In general, as the binding constant for the cobalt(II) ion-chelating agent complex is increased, a value is reached wherein the chelating agent binds the cobalt(II) ion sufficiently strongly to prevent formation of the lavender cobalt(II) ion-gallocyanine complex. The data in Table III illustrates that at a pK of about 10, the chelating agent binds the cobalt(II) ion sufficiently strongly to preclude an interaction between cobalt(II) ion and gallocyanine. Histidine, having a pK of 7.3 with cobalt(II) ion is an exception to this general pattern. The data in Table III also illustrate that if the cobalt(II) ion is bound to the chelating agent too strongly (i.e., a pK of 11 or greater), the sensitivity to externally added cations is diminished or lost.

For cobalt(II) ion-chelating agent complexes having a pK of about 10 to about 11, responses to externally added sodium and calcium ions were small. Two chelates (i.e., BTFA and TTFA), however, demonstrated a dramatic response to added magnesium ions. Accordingly, an assay is available to correlate urine cation concentration to urine specific gravity. In a related experiment wherein the concentration of BTFA in the reagent composition was lowered from 10 mM to 5 mM, the sensitivity to all three of the test cations (i.e., sodium, calcium and magnesium) was improved. Therefore, increasing the ratio of cobalt(II) to chelating agent improves the response of the reagent composition to added cations.

Experiments also were performed using an ion exchange material as the complexing agent. In these experiments, performed at pH 5, the polyvalent metal ion was ferric ion and the indicator was diphenyl carbazone. Diphenylcarbazone is orange in color in the absence of ferric ion. In the presence of ferric ion, the ferric ion-diphenylcarbazone complex is an intense blue color. In these experiments, each of the following seven ion exchange papers were treated sequentially, first with a solution including ferric ion, then with a diphenylcarbazone solution:

SULFONIC ACID RESIN-LOADED SA-2;
GLASS FIBER, RESIN LOADED WITH POLYSTYRENESULFONIC ACID GF/SE 30;
CELLULOSE PHOSPHATE C/P 30;
CELLULOSE PHOSPHATE P/81;
CARBOXYMETHYLCELLULOSE C/CM 30;
DIETHYLAMINOETHYLCELLULOSE C/DE 30; and VA, QUAT. AMMONIUM GF/QA 30.

All the ion exchange papers are available commercially from WHATMAN LTD., Maidenhead, Kent, England.

A test strip including ferric ion and diphenylcarbazone incorporated into the sulfonic acid resin-loaded paper responded to contact with a 2% by weight aqueous solution of sodium chloride with a large color transition from orange to intense red-purple. Identical test strips provided a less intense color transition after contact with aqueous solutions including magnesium ions or calcium ions. Visually, the test strips readily distinguished water from a low specific gravity urine, and distinguish a low specific gravity urine from a medium specific gravity urine.

To show the new and unexpected results achieved by using a reagent composition of the present invention in a method of determining the specific gravity of a test sample, color space plots were prepared from assays using dry phase test strips comprising a test pad incorporating a reagent composition of the present invention into a filter paper matrix. The color space plots were obtained by contacting standardized solutions of known specific gravity with the dry phase test strips including the present reagent composition incorporated into a filter paper carrier matrix.

In general, a color space plot includes three axes, the L*, A* and B* axes. The values of L* plotted on the vertical axis are a measure of the intensity of color, whereby a large L* value denotes a light color and L*=0 denotes a completely black color. The horizontal A* axis is a measure of the color transition from green to red, whereby the more positive the A* value, the more red the color, and analogously, the more negative the A* value, the more green the color. Similarly, the third axis, B*, is a measure of the color transition from blue to yellow, whereby the greater the value of B*, the more yellow the color, and analogously the smaller the value of B*, the more blue the color.

The color space difference ($\Delta E$) is calculated from the following equation (Eq. 2):

$$\Delta E = \sqrt{(L_1^* - L_2^*)^2 + (A_1^* - A_2^*)^2 + (B_1^* - B_2^*)^2} \qquad \text{Eq. 2}$$

wherein:

$L_1^*$, $A_1^*$, and $B_1^*$ are the color space values determined for a first standardized solution of known specific gravity;

$L_2^*$, $A_2^*$ and $B_2^*$ are the color space values determined for a second standardized solution of known specific gravity having a different specific gravity from the first standardized solution; and $\Delta E$ is the color space difference between the color space plots of the first and second standardized solutions.

The color space difference ($\Delta E$) is the straight line distance between two points in a three-dimensional color space plot. Theoretically, a color space difference of one (1) unit is the smallest color space difference the human eye can distinguish. However, because of the inherent differences between the visual capabilities of individuals, a color space difference ($\Delta E$) of about 3 units is required in order to practically and confidently distinguish between colors.

The L*, A* and B* values plotted on the color space plots are calculated from the different reflectance measurements taken at sixteen different wavelengths evenly spaced between 400 nm (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values, X, Y and Z. Values L*, A* and B* are calculated from the X, Y and Z tristimulus values using the following equations:

$$L^* = 116 \times [(Y/Y_o)^{\frac{1}{3}} - 16)] \qquad \text{(Eq. 3)}$$

$$A^* = 500 \times [(X/X_o)^{\frac{1}{3}} - (Y/Y_o)^{\frac{1}{3}}] \qquad \text{(Eq. 4)}$$

$$B^* = 200 \times [(Y/Y_o)^{\frac{1}{3}} - Z(Z/Z_o)^{\frac{1}{3}}] \qquad \text{(Eq. 5)}$$

wherein:

$X_o$, $Y_o$ and $Z_o$ are the tristimulus values for perfect white (i.e., reflectance=100% at all wavelengths), and X, Y and Z are the tristimulus values calculated as described above from the sixteen wavelengths between 400 nm and 700 nm.

From the color space plots, the color space differences ($\Delta E$) were calculated, and are summarized and discussed in more detail hereinafter. In interpreting the data to be presented, a term such as $\Delta E$ (1.007–1.016) is the color space difference between specific gravity assays for standardized urine solutions having a specific gravity of 1.007 and 1.016. Similarly, the term $\Delta E$ (0–5) is the color space difference between assays of standardized solutions having a cation concentration of 0 mM and 5 mM respectively. The terms $\Delta E$ (0–8) and $\Delta E$ (0–340) are analogously defined.

To demonstrate the unexpected results provided by the present invention, a reagent composition was prepared, then utilized in assays for specific gravity. The results are set forth in Examples 2 and 3 and Table IV. The following Example 2 illustrates a dry phase specific gravity assay utilizing a reagent composition wherein the complexing agent is an ion exchange material.

EXAMPLE 2

Dry Phase Test Strip Incorporating a Reagent Composition Including an Ion Exchange Material as the Complexing Agent Five milliliters of aqueous biphthalate buffer (0.2 M, pH 4.0) was admixed with 5 milliliters (ml) of aqueous ferric chloride (4 mM). The resulting solution was incorporated into a sulfonic acid resin-impregnated paper (WHATMAN SA-2), then the resulting treated paper was dried by conventional procedures. The dried paper incorporating the ferric chloride (polyvalent metal ion), the biphthalate buffer (buffer) and the complexing agent (sulfonic acid resin ion exchange material) then was dipped into an ethanolic solution of the indicator pyrocatechol violet (2 mM). The resulting paper was dried again by conventional procedures, then cut into test strips. The test strips have incorporated therein a reagent composition of the present invention.

Individual test strips were dipped into standardized sodium chloride (340 mM), calcium chloride (5 mM) and magnesium chloride (8 mM) solutions, and into standardized urine solutions having a specific gravity of 1.000 to 1.023. The standardized urine solutions had the following properties:

|  | LOW | MEDIUM | HIGH |
|---|---|---|---|
| Specific Gravity | 1.007 | 1.016 | 1.023 |
| Sodium, meq/L | 44 | 135 | 130 |
| Calcium, meq/L | 2.6 | 7.8 | 11.0 |
| Magnesium, meq/L | 1.4 | 4.2 | 10.8 |
| Phosphate, mM | 11.2 | 14.6 | 20.3 |

The resulting color transition of each test strip was determined and converted into $\Delta E$ units by standard procedures known in the art. The $\Delta E$ units for these experiments are summarized in TABLE IV. Essentially identical results were obtained for test strips incorporating 5 ml of 2 mM aqueous ferric chloride.

TABLE IV $\Delta E$ DIFFERENCES FOR TEST STRIPS UTILIZING AN ION EXCHANGE MATERIAL AS THE COMPLEXING AGENT

| Test Sample | $\Delta E$ values |
|---|---|
| Sodium Chloride (340 mM) vs. water | $\Delta E$ (0–340) = 30 |
| Calcium Chloride (5 mM) vs. water | $\Delta E$ (0–5) = 6 |
| Magnesium Chloride (8 mM) vs. water | $\Delta E$ (0–8) = 2 |
| Urine Specific Gravity | $\Delta E$ (1.000–1.007) = 17 |
|  | $\Delta E$ (1.007–1.016) = 4 |
|  | $\Delta E$ (1.016–1.023) = 3 |

In accordance with the method and Composition of the present invention, the data presented in TABLE IV illustrate that a reagent composition including an ion exchange material as the complexing agent provide a dry phase assay for specific gravity wherein the color space differences generally are at, or above, the minimum human detectable limit of approximately three ΔE units. Generally, the color space difference values are at or above 3, therefore a color change is discernible by the human eye, and the assayer easily can differentiate between urine samples having specific gravities differing by as little as 0.006 in the specific gravity range of about 1.000 to about 1.023, and up to 1.035. It should be noted that the amount of cations in urine is directly proportional to the color change, or ΔE.

Specifically, the test strips showed an excellent sensitivity to sodium ions in the range of 0 mM to 340 mM that is readily perceptible to the human eye (ΔE=30). The test strips also showed a sensitivity to calcium ions in the range of 0 mM to 5 mM (ΔE=6) that is perceptible to the human eye, thereby allowing an assayer to distinguish between test samples including 0 mM or 5 mM calcium ions. An assayer however would have more difficulty discerning between a solution that is 0 mM and 8 mM in magnesium ions. Overall, the results illustrated in Table IV show that the reagent composition has a sufficient sensitivity with respect to cations to assay for specific gravity.

The test strips also showed an excellent sensitivity to different urine specific gravities over the specific gravity range of 1.000 to 1.023. In each of the three experiments the ΔE value exceeded the minimal visually detectable limit. It has been theorized that the test strips did not more clearly distinguish between the medium and high specific gravity urine samples because the sodium ion concentrations in the two urine samples was essentially the same. However, an assayer can readily determine whether the urine specific gravity in the low, medium or high specific gravity range. An assayer can detect and measure a urine specific gravity because the color space differences exhibited at or above the minimum detectable level of 3 color space units.

As previously stated, the complexing agent included in the reagent composition can be a relatively low molecular weight chelating agent. The following Example 3 illustrates a wet phase specific gravity assay utilizing a reagent composition of the present invention wherein the complexing agent is a chelating agent.

EXAMPLE 3

Wet Phase Assay Utilizing a Chelating Agent as the Complexing Agent

One part by volume of each of the following ingredients was admixed to provide a reagent composition of the present invention:
  HEPES (0.5 M, pH 8.0)—buffer
  Benzoyltrifluoroacetone (1.0 mM)—complexing agent
  Cobaltous chloride (1.0 mM)—polyvalent metal ion
  Gallocyanine (1.0 mM)—indicator
  Distilled Water.

The resulting reagent composition was blue in color. An aqueous solution of magnesium chloride then was added to a portion of the reagent composition. The resulting solution, including 6.4 mM magnesium ions, underwent a large color transition from blue to pink lavender. Similarly, other portions of the reagent composition were made 4 mM in calcium chloride and 340 mM in sodium chloride, respectively. The color transitions were from blue to lavender upon addition of the calcium chloride or sodium chloride. The reagent composition of Example 3 therefore demonstrated a spectacular response to magnesium ions, and a detectable response to calcium and sodium ions.

As a result, a reagent composition including a complexing agent, a polyvalent metal ion and an indicator differentiates and measures the specific gravity of a test sample, allowing the semiquantitative specific gravity assay of test samples. The present reagent compositions provide an important and useful benefit of providing a specific gravity assay that relies upon the formation of a colored complex, as opposed to relying upon a pH change. Therefore, the reagent composition can be buffered to preclude assay inaccuracies due to urine pH. As illustrated above, the indicator included in the present reagent composition responds directly to the cation concentration of the test sample, is essentially independent of pH, and provides a semiquantitative specific gravity assay.

It should be understood that those skilled in the art of designing test kits are able to design an optimal test strip incorporating a sufficient amount of a particularly effective reagent composition to permit the differentiation and measurement of test sample specific gravities differing by as little as 0.006, because an assay utilizing the method and composition of the present invention exhibit a color space difference of at least 3 units. This ΔE value is sufficient for detection by the human eye, and is easily detected by present day colorimeters or spectrophotometers. Similarly, the method and composition of the present invention provide an accurate specific gravity assay regardless of varying amounts of nonionic components, such as glucose or albumin, found in the test sample, as long as a sufficient number of cations are present in the test sample to cause a color transition that can be correlated to test sample specific gravity.

In accordance with another important feature of the present invention, full color development of a test strip including a present reagent composition occurs within about 10 seconds to about 60 seconds after contacting the test strip with the test sample. Maximum color development occurs after about 30 seconds of contact. However, acceptable and trustworthy specific gravity assay results are achieved when the test strip is examined for a color change about 15 seconds after contact with the test sample. Such a short time for full color development of the test strip is an additional advantage of the reagent composition of the present invention. In addition, the color transition is sufficiently stable such that an accurate assay results from examining the test strip one or more hours after contacting the test sample. Therefore, test strips incorporating the reagent composition of the present invention can be used to obtain fast and accurate specific gravity assays.

Overall, the present reagent composition incorporated into a suitable carrier matrix, such as filter paper, improves color differentiation between test samples having specific gravities differing by as little as 0.006 for test samples having a specific gravity of about 1.000 to about 1.035, and therefore provides excellent sensitivity to the specific gravity of aqueous test samples. In addition to excellent sensitivity, the method and composition of the present invention provide full color development and accurate assay results in a relatively short time.

Therefore, in accordance with an important feature of the present invention, accurate and reliable semiquantitative assays for the specific gravity of urine and other liquid test samples can be performed by utilizing a reagent composition comprising a complexing agent, a polyvalent metal ion and an indicator. The reagent composition provides sufficient color differentiation between test samples having different specific gravities, and is essentially independent of pH, thereby improving assay sensitivity.

Obviously, many modifications and variations of the invention as hereinbefore set forth can be made without departing from the spirit and scope thereof and therefore only such limitations should be imposed as are indicated by the appended claims.

What is claimed is:

1. A composition capable of exhibiting a detectable and measurable color transition in response to the cation concentration of an aqueous test sample, said composition consisting essentially of:
   (a) a polyvalent metal ion having a valence of at least two;
   (b) a complexing agent capable of complexing with the polyvalent metal ion, said complexing agent selected from the group consisting of a polyelectrolyte, an ion exchange material, a chelating agent, and mixtures thereof;
   (c) an indicator capable of interacting with the polyvalent metal ion to provide a color transition, said indicator selected for the group consisting of 1,10-phenanthroline, bathophenanthroline, 2,2'-dipyridyl, ripyridyl-s-triazine, disodium pyrocatechol-3,5-disulfonate, diemthylglyoxime, rubeanic acid, eriochrome black T, rhodizonic acid, calmagite, gallocyanine, diphenylthiocarbazone, diphenylcarbazone, potassium ferricyanide, pyrocathechol violet, 5-methyl-1,10-phenanthroline, 5-nitro-1,10-phenanthroline, 3-(4-phenyl-2-pyridyl)-5,6-diphenyl-1,2,4-triazinetrisulfonic acid trisodium slat, 3-(2-pyridyl)-5,6-diphenyl-1,2,4-triazine, 3-(2-pyridyl)-5,6-diphenyl-1,2,4-triazinedisulfonic acid disodium slat, henyl-2-pyridyl ketoxime, 4'-phenyl-2,2',2"-terpyridine, 2,2',2"-terpyridine, 4,4',4"-triphenyl-2,2',2"-terpyridine, 2,3,5,6-tetrakis (2'-pyridyl)pyrazine, 2,2'-biquinoline, bis-cyclohexanone oxaldihydrazone, 2,4-bis(5,6-diphenyl-1,2,4-triazine-3-yl)pyridine, 2,4-bis(5,6-diphenyl-1,2,4-triazin-3-yl)pyridinetetra-sulfonic acid tetrasodium salt, 4,4'-dihydroxy-2'-biquinoline, 4,7-dihydroxy-1,10-phenanthroline, 4,4'-dimethyl-2,2'-bipyridine, 2,9-dimethyl-1,10-phenanthroline, 2,9-dimethyl-4,7-diphenyl-1,10-phenanthorline, 2,9-dimethyl-4,7-diphenyl-1,10-phenanthrolinedisulfonic acid, 4,7-dimethyl-1,10-phenanthroline, 5,6-dimethyl-1,10-phenanthorline, and mixtures thereof; and
   (d) a carrier comprising water, a water miscible alcohol, or a mixture thereof.

2. The composition of claim 1 wherein the polyvalent metal ion is present in a concentration of about 0.02 to about 5 millimoles per liter of the composition.

3. The composition of claim 1 wherein the polyvalent metal ion is selected from the group consisting of ferric ion, ferrous ion, calcium ion, magnesium ion, cobalt(II) ion, cobalt(III) ion, cupric ion, mercuric ion, stannic ion, nickel(II) ion, lead(II) ion, manganese(III) ion, cadmium(II) ion, zinc(II) ion, molybdenum(V) ion, chromium(IV) ion, vanadium(III) ion, and mixtures thereof.

4. The composition of claim 1 wherein the complexing agent has a partial negative charge or a full negative charge.

5. The composition of claim 1 wherein the complexing agent is present in a concentration of about 0.04 to about 0.2 millimoles per liter of the composition.

6. The composition of claim 1 wherein the complexing agent is a polyelectrolyte having a sufficient number of negatively-charged sites to complex with the polyvalent metal ion.

7. The composition of claim 6 wherein the polyelectrolyte is selected from the group consisting of a poly(vinyl sulfate); a poly(vinyl sulfonate); a poly(styrenesulfonate); a maleic acid-methyl vinyl ether copolymer; a polyvinylpyrrolidone; a polyethylenimine; a polymeric secondary amine; a polymeric tertiary amine; a polypeptide including cysteine, glycine, histidine, leucine or isoleucine; and mixtures thereof.

8. The composition of claim 1 wherein the complexing agent is an ion exchange material selected from the group consisting of cellulose phosphate, carboxymethylcellulose, diethylaminoethylcellulose, a paper loaded with a sulfonic acid resin, a glass fiber including sulfonic acid groups, and combinations thereof.

9. The composition of claim 1 wherein the complexing agent is a chelating agent selected from the group consisting of a polycarboxyalkylamine; aminotris(methylene phosphoric acid); hydroxyethylidene diphosphoric acid; hexamethylenediaminetetra(methylene phosphonate); nitrilopropionic acid; 1-hydroxyethane. diphosphonic acid; a polycarboxylic acid; a salt of a polycarboxylic acid; a polyhydroxy compound; a lignosulfonate; a glucoheptonate; dimethylglyoxime; a salicylate complex; ethylenediamine; histidine; proline; a proline derivative; phenylalanine; benzoyltrifluoroacetone; thenoyltrifluoracetone; a dithionate derivative; a polyethyleneamine; a 2,4-pentanedione derivative; a dipyridine derivative; triethylanepyridine amine; a thiocrown ether; a triphenylphosphine; and mixtures thereof.

10. The composition of claim 9 wherein the polycarboxyalkylamine is selected from the group consisting of ethylenediaminetetraacetic acid, ethylenediaminediacetic acid, N-(2-hydroxyethyl)ethylenediaminetriacetic acid, cyclohexylenediaminetetraacetic acid, nitrilotriacetic acid, iminodiacetic acid, ethylenediaminediacetic dipropionic acid, hydroxyethyliminodiacetic acid, diethylenetriaminepentaacetic acid, ethylenebis(oxyethylenenitrilo)tetraacetic acid, N-(2-acetamido)iminodiacetic acid, and mixtures thereof.

11. The composition of claim 1 wherein the indicator is present in a concentration of about 0.02 to about 4 millimoles per liter of the composition.

12. The composition of claim 1 wherein the carrier further comprises 0% to about 20% by weight of the carrier of an organic solvent.

13. The composition of claim 1 further comprising:
   (e) 0 to about 200 millimoles per liter of a buffer.

14. The composition of claim 13 wherein the composition is buffered to a pH of about 4 to about 9.

15. The composition of claim 13 wherein the buffer is selected from the group consisting of acetate; BICINE; phthalate; borate; trichloracetate; sulfosalicylate; phosphate; tartarate; citrate; succinate; maleic acid; 2,2-bis(-hydroxymethyl)-2,2', 2"-nitrilotriethanol; 3,3-dimethylglutaric acid; 3-N-morpholinopropanesulfonic acid; malonic acid; 1,3-bis[tris(hydroxymethyl)methylamino]propane; tris(hydroxymethyl)aminomethane; N-(carbamoylmethyl)taurine; tris(hydroxymethyl)aminomethane-maleic acid; tris(hydroxymethyl)aminomethane-malonic acid; 3-N-(trishydroxymethyl)- methylamino-2-hydroxypropanesulfonic acid; 2-([tris(-hydroxymethyl)methyl]amino)-ethanesulfonic acid; 1,4-piperazinebis(ethanesulfonic acid); 4-morpholinoethanesulfonic acid; N-2-hydroxyethylpiperazine-N'-2-ethanesulfonic acid; and mixtures thereof.

16. The composition of claim 1 wherein the polyvalent metal ion is selected from the group consisting of lead(II) ion, ferric ion, cobalt(II) ion, ferrous ion, magnesium ion, and mixtures thereof; and the indicator is selected from the group consisting of calmagite, rubeanic acid, dithizone, diphenylcarbazone, diphenylthiocarbazone, gallocyanine, eriochrome black T, 2,2'-dipyridyl, tripyridyl-s-triazine, rhodizonic acid, pyrocatechol violet, 1,10-phenanthroline, bathophenanthroline, disodium pyrocatechol-3,5-disulfonate, dimethylglyoxime, and mixtures thereof.

* * * * *

UNITED STATES PATENT AND TRADEMARK OFFICE
CERTIFICATE OF CORRECTION

PATENT NO. : 5,302,531

DATED : April 12, 1994

INVENTOR(S) : Robert Bauer

It is certified that error appears in the above-identified patent and that said Letters Patent is hereby corrected as shown below:

Col. 29, line 28, "ripyridyl-s-triazine" should be --tripyridyl-s-triazine--

Col. 29, line 35, "nyl-1,2,4-triazinetrisulfonic acid trisodium slat, 3-" should be --nyl-1,2,4-triazine, 3-(4-phenyl-2-pyridyl)-5,6-diphenyl-1,2,4-triazinetrisulfonic acid trisodium salt, 3--

Col. 29, line 38, "disodium slat, henyl-2" should be --disodium salt, phenyl-2--

Col. 29, line 45, "4,4'-dihydroxy-2'biquinoline" should be --4,4'-dihydroxy-2-2'-biquinoline,--

Signed and Sealed this

Tenth Day of June, 1997

Attest:

BRUCE LEHMAN

Attesting Officer        Commissioner of Patents and Trademarks